United States Patent [19]

Doellgast

[11] Patent Number: 4,668,621
[45] Date of Patent: May 26, 1987

[54] DETECTING BLOOD CLOTTING FACTORS WITH IMMOBILIZED FIBRINOGEN AND LABELED FIBRINOGEN

[75] Inventor: George J. Doellgast, Winston-Salem, N.C.

[73] Assignee: Wake Forest University, Winston-Salem, N.C.

[21] Appl. No.: 725,460

[22] Filed: Apr. 22, 1985

[51] Int. Cl.⁴ .................... G01N 33/53; G01N 33/58; G01N 33/86
[52] U.S. Cl. ........................................ 435/13; 435/28; 435/174; 435/180; 435/184; 435/188; 435/214
[58] Field of Search ................ 435/13, 184, 188, 214, 435/28, 174, 180

[56] References Cited
U.S. PATENT DOCUMENTS 3,778,352 12/1973 Bishop .................................... 435/13
3,960,669 6/1976 Innerfield .............................. 435/13
4,011,142 3/1977 Jacobi .................................... 435/13
4,046,635 9/1977 Moroz .................................... 435/13
4,216,291 8/1980 Collen ................................ 435/13 X
4,463,090 7/1984 Harris ................................ 435/13 X

OTHER PUBLICATIONS

Chemical Abstracts, 94:169108t, (1981).

Primary Examiner—Sidney Marantz
Attorney, Agent, or Firm—Bertram I. Rowland

[57] ABSTRACT

Assays and reagents for the direct determination of blood factors, as well as complementary methods and reagents for determining such blood factors and haptens, antigens and receptors. The methods involve clot formation due to thrombin activated fibrin formation from insolubilized fibrogen and labeled solubilized fibrogen. Insolubilized label can be determined prior to or after clot formation.

10 Claims, No Drawings

DETECTING BLOOD CLOTTING FACTORS WITH IMMOBILIZED FIBRINOGEN AND LABELED FIBRINOGEN

This invention was made with U.S. Government support under Grant No. 2-RO1-AM21940-04A1 awarded by the National Institutes of Health. The U.S. Government may have certain rights in this invention.

BACKGROUND OF THE INVENTION

1. Field of the Invention

There is substantial interest in the ability to detect the presence of various blood factors involved with the formation or inhibition of clotting. Two of the classical procedures involve the use of genetically deficient plasmas or mixtures of coagulation factors deficient in one essential factor and in one case assaying the formation of a clot using a variety of physical techniques. In the other case specific synthetic substrates for individual coagulation factors are employed, where such factors are enzymes or modulate the activity of enzyme factors. These techniques suffer from numerous deficiencies, in being expensive, requiring technical skills, in performing the assay, and difficulties in the obtaining and/or preparation of reagents.

There is, therefore, a significant need for providing rapid and efficient assays capable of automation for the detection of blood factors. In addition, despite the large number of immunoassays which are presently available with varying protocols and labels, there is still interest in providing assays which allow for high sensitivity, rapidity, and which are capable of detecting a wide variety of analytes of interest.

2. Description of the Prior Art

CRC Handbook Series in Clinical Laboratory Science (Seligson, ed.-in-chief), Section I: Hematology, Vol. III (Schmidt, ed.), 1980, concisely summarizes assays of individual factors. The use of synthetic substrates is described in Fareed et al., *Clin. Chem.* (1983) 29:225–236. The following report that fibrinogen binds extremely tightly to plastic surfaces: Parsons, *Meth. Enzymology* (1981) 73:224–239; Pesce, *Biochim. Biophys. Acta* (1977) 492:399–407; and Morrisey, *Ann. N.Y. Acad. Sci.* (1977) 283:50–64. The following report that fibrinogen bound to plastic may serve as a matrix for fibrin deposition: Ihlenfeld and Cooper, *J. Biomed. Mat. Res.* (1979) 13:577–591 and Packman et al., *J. Lab. & Clin. Med.* (1969) 73:686–697.

SUMMARY OF THE INVENTION

Novel methods and compositions are provided based on the enzyme catalyzed insolubilization of labeled fibrinogen by formation of labeled fibrin in the presence of insolubilized fibrinogen, also subject to enzyme catalyzed fibrin formation, whereby a labeled fibrin-insolubilized fibrin complex is formed at the site of the insolubilized fibrinogen. The method can be used for the detection of a wide variety of analytes, being capable of detecting directly blood factors involved in clot formation or inhibition of clot formation, and indirectly, a wide variety of analytes, including haptens, antigens, and receptors, particularly antibodies.

DESCRIPTION OF THE SPECIFIC EMBODIMENTS

The subject method involves fibrinogen bound to a solid substrate, labeled fibrinogen, thrombin or prothrombin except when the assay is for thrombin, and such other ancillary reagents associated with the formation of fibrin by thrombin and the detection of the analyte of interest. Either an end point determination may be employed, where a plateau value is observed as an analogue of clot formation, or some intermediate stage may be selected where a single or plurality of determinations may be made to in effect provide a rate determination for complex formation. Once the complex has been formed, the determination of amount of label present in the complex may be readily determined in accordance with the nature of the label.

Various protocols may be employed which will depend upon the analyte. Different analytes will require different protocols and reagents. Common to all the protocols will be fibrinogen bound to a support and labeled fibrinogen, by itself, or in combination with unlabeled fibrinogen.

Assays for thrombin will not require additional reagents for clot formation, although other reagents could be added. Where the analyte activates or inhibits thrombin, then thrombin would be added to the assay medium for such analyte.

Where a clotting factor is the analyte, then it will be necessary to include the other factors which the analyte requires to produce thrombin from prothrombin, as well as prothrombin, in the assay medium. Similarly, where the analyte activates or inhibits a particular factor, then that factor would be included with the additional factors necessary for cleavage of prothrombin to thrombin. The mixture of factors could be diluted plasmas deficient in the factor of interest, or mixture of purified factors lacking the factor of interest to complete the coagulation cascade.

Finally, conjugates of analyte to an agent involved in clotting or modulating clotting could be employed. The agent could be prothrombin, thrombin, another clotting factor other than fibrinogen, or an activator or inhibitor of thrombin or other clotting factor. The agent has an effect on clotting as a result of complex formation between analyte and its complementary binding member affecting the rate of clot formation. (By complex formation is intended the non-covalent binding of a ligand and its complementary receptor, where the ligand and receptor define a specific binding pair.)

The various reagents would be mixed and incubated for a sufficient time for reaction to occur either at an intermediate stage or to clot formation. The liquid phase would then be removed, the solid phase washed to remove any non-specifically bound label and the amount of label bound to the surface determined as an indication of the amount of analyte present.

As already indicated, the subject assays can be performed either "directly" or "indirectly," where indirectly will involve a competitive or secondary interaction affecting production of thrombin or thrombin activity, while directly intends that the analyte of interest has a direct effect, either activation or inhibition, on production of thrombin or thrombin activity.

The first assays to be considered in the direct mode are those assays involving blood factors. The protocol of the assay will vary somewhat depending upon whether the factor is a component of the extrinsic or intrinsic pathway or is involved with both pathways, being referred to as the common pathway. The factors involved in the intrinsic pathway include VIII, IX, XI and XII, while the factors involved in the extrinsic pathway include III (tissue factor) and VII. Those factors involved in the common pathway include V, X, XIII, I (fibrinogen) and II (prothrombin).

Human clotting factor deficient plasmas are commercially available, where the plasma lacks a specific factor or a group of factors. These plasmas may be used in the assays and as standards for comparison with plasmas suspected of having a genetic deficiency or other reason for being incompetent in having a clotting factor capable of activation. Those plasmas which are believed to be deficient in the factors of the intrinsic pathway (VIII, IX, XI, and XII) could be stimulated by Celite or kaolin plus lipid while plasma deficient in the extrinsic pathway (VII) could be stimulated by tissue factor (thromboplastin, III). It will also be possible to prepare mixtures of purified factors minus the factor of interest using in some cases enzymes which can activate individual factors such as snake venom factor X activator or factor V activator. This approach will be particular desirable when measuring factors of the common pathway (X, II, V), since fewer purified factors should be required.

In many instances, it will not be necessary to use factors of the same species as the species of the analyte, since in most instances, factors from different species will provide cross-activation. Thus, the factors from such diverse species as mouse, rabbit, rat, monkey, cow, human or the like, may find use, where the factor or factors may be titrated with samples having known amounts of activity as to the various clotting factors and the utility of the particular species determined. Thus, it will not be necessary to use human factors in the subject assay for human analytes, although this could prove to be desirable.

Not only can the subject technique be used with specific clotting factors, but also with naturally occurring or synthetic materials which may activate or inhibit one or more factors. Thus, one can also use the subject methodology for measuring the presence of materials which modulate the activity of one or more of the blood clotting factors.

Where one is concerned with determining the activity of a particular factor in a sample, one would take a blood sample, dilute it to one or more, usually a plurality of dilutions, and add it to plasma deficient in the factor to be assayed. In this manner, the contribution of the sample to the clot formation will be negligibly small except for the analyte, so that the observed effect will solely be the result of the particular factor of interest in the plasma, or the contribution can be related to standards. Similarly, where one wishes to investigate an endogenous activator or inhibitor which may be present in a physiological sample, one would add dilutions of the plasma to a medium containing all of the factors, where the factors are present in the medium in sufficient amount to substantially overwhelm the contribution from the sample. Alternatively, where the particular material to be analyzed may be substantially concentrated and freed of other factors involved in the clotting pathway, the concentrate may then be used and the amount of the various factors present in the medium may range from a substantial dilution of normal plasma to a concentrate.

The various components may be brought together simultaneously or consecutively. Preferably, the sample and labeled fibrinogen in a medium having the appropriate factors would be combined with the support bound fibrinogen, followed by the addition of an activating agent, such as calcium. The mixture may then be incubated for sufficient time for reaction to occur. Under the circumstances, one can carry out the reaction as a rate or endpoint, the endpoint being particularly desirable. It should be appreciated that there is a period of time where there would no observable signal present based on label bound to the surface and then a very rapid increase of label bound to the surface with a value reached which is off-scale. Thus, by having varying concentrations of the sample, one can look at the highest concentration which is the first concentration to give the maximum value or a value immediately below the maximum value. This value may then be translated into the concentration or active amount of a particular factor, activator or inhibitor.

Of equal importance is the fact that the subject method provides for a simple technique for detecting any analyte, by allowing for complex formation to modulate thrombin activity. Thus, the use of the combination of thrombin, support bound fibrinogen and labeled fibrinogen can be coupled to any system which allows for modulation of thrombin activity. A wide variety of systems have been developed and can find use with the subject detection system.

In one embodiment, one would link a thrombin activator or inhibitor with the analyte of interest, where binding of antibody or other receptor to the analyte of interest would inhibit the thrombin activator or inhibitor (modulator) from interacting with thrombin. One could then carry out a competitive assay between the conjugate and the analyte for receptor to the analyte, followed by combining the competitive assay medium with known amounts of thrombin and labeled fibrinogen in the presence of bound fibrinogen. Where one is solely concerned with whether the analyte is present below or above a particular threshold concentration, one could readily determine whether clotting occurred within a predetermined time, as indicative of the presence of the analyte above the threshold concentration. Where a quantitative determination is desired of the amount of analyte, one could serially carry out the assay at varying concentrations of the sample and determine the concentration at which the plateau value or the value immediately below the plateau is obtained as indicative of the concentration of the analyte.

Alternatively, one could conjugate a factor in the clotting cascade (e.g., thrombin, Xa, VIIa, tissue factor) with analyte, particularly haptenic analyte and perform a homogeneous or heterogeneous assay. The homogeneous assay would involve binding of antibody to the factor modulating its activity. The heterogeneous assay would involve binding of the factor conjugate to a support containing receptor for the analyte. One would perform a competitive assay between analyte and analyte conjugated to factor and then remove the supernatant. The amount of bound factor would then be determined by assay for specific factor bound to the solid phase. The amount of bound factor would be inversely proportional to the amount of analyte in the sample and by employing the technique described above, one could qualitatively or quantitively determine the amount of analyte in the sample. A similar technique could employ an affinity column, where the amount of factor held up in the column would be inversely proportional to the amount of analyte in the sample. The factor chosen for conjugation to the analyte would depend on the sensitivity desired for the assay. Thus, factors VIIa and III (tissue factor) can be detected in the picogram/ml range, while thrombin can be detected in the nanogram/ml range. The ability to choose a sensitivity range for assay of any analyte, with a single method for detecting the endpoint of the assay, is one of the significant advantages of this method.

Alternatively, one could prepare monoclonal antibodies specific for individual factors, which inhibit their activity. By conjugating the antibody and analyte and having a competition between the analyte of the antibody conjugate and analyte in the sample for the reciprocal member of the specific binding pair bound to a surface, the amount of inhibitory antibody in the supernatant medium would be related to the amount of analyte in the sample. The supernatant would then be combined with the detection system for determining the amount of analyte in the sample.

One could also use an ELISA mode, whereby a factor conjugate is employed which competes with analyte for the reciprocal binding member, which is bound to support. The amount of factor conjugate which is bound to the surface or is retained in the supernatant could then be determined employing the detection system.

As thrombin inhibitors or activators, compounds which could find use include benzamidine, anti-thrombin III, serine protease inhibitors, $\alpha_2$-macroglobulin, $\alpha$1-antitrypsin, C-1 esterase inhibitor.

As a label for the fibrinogen, any molecule may be employed which does not interfere with clotting but allows for detection. A wide variety of labels have found use, such as enzymes, radionuclides, fluorescers, chemiluminescers, enzyme substrates and co-factors, enzyme inhibitors, and the like. The labels may be bound either directly or indirectly to the fibrinogen, where various bridging groups may be employed, such as antibodies, hapten-receptors, e.g., biotin-avidin, polynucleotides, or the like. Numerous patents have issued describing the use of these various materials, the following being illustrative of the group: U.S. Pat. Nos. Re 29,169; Re 29,955; 3,654,090; 3,690,834; 3,817,837; 3,867,517; 3,935,074; 3,975,511; 3,996,345; and 4,020,151.

The fibrinogen bound to the support can be present in a variety of ways, conveniently bound to walls of microtiter wells, walls of capillaries, bound to particles, e.g., magnetic particles, polysaccharides, or the like, or other surface which allows for the clot to be localized at a site where the label can be measured. Of particular interest are microtiter plates, where the signal may be measured in a microtiter plate reader. These readers are now commercially available.

The fibrinogen may be coated onto the surface of the support at varying concentrations. Conveniently, a solution of fibrinogen may be sprayed, coated, or applied by any other convenient means to the surface and allow it to dry. The amount of fibrinogen would generally be about 1 to 10 $\mu$g/well. Any conveniently buffered solution may be employed, generally at a pH in the range of about 6 to 9. After the surface has been coated, it may be allowed to dry under ambient or slightly elevated temperature conditions, with or without vacuum. To substantially reduce or eliminate non-specific binding to the surface, the surface may then be coated with an inert protein, such as serum albumin, where the surface would be contacted with a solution having from about 1 to 20 mg/ml of protein for sufficient time for the protein to bind to the surface, followed by washing and mild drying. The fibrinogen should then be maintained in a moderately humid environment to ensure its continued activity, which can be achieved by maintaining a small amount of water in contact with the surface, for example, by sealing the wells until immediately prior to use.

The assay may be carried out under mild temperature conditions, generally ranging from about 10° to 40° C., more usually from about 20° to 37° C. The concentration of the various reagents will vary widely, depending upon the particular protocol, what is being measured, the concentration range of interest of the analyte, whether a qualitative or quantitative determination is required, the time for the assay, and the like. Thus, the assay time may range from about 1 min to 6 hr, more usually from about 1 min to 2 hr. Incubation times may vary from about 1 min to 2hr or more. The media employed will normally be aqueous media, where the small amounts of polarorganic solvents may be included, usually less than 40 volume percent, more usually less than about 10 volume percent. The solutions will normally be buffered at a pH in the range from about 6 to 9, more usually from about 7 to 8.5. Various buffers may be employed, such as phosphate, Tris, or the like, which do not inhibit coagulation reactions.

The subject method can be used with any type of ligand, haptenic or antigenic, receptors, polynucleotides, or the like. Besides the blood factors which have been described previously, drugs, hormones, enzymes, lymphokines, neurotransmitters, membrane proteins, regulatory proteins, growth factors, or the like may all be of interest.

To aid in use of the subject invention, kits can be provided containing the various reagents. In preferred ratios, so as to optimize the sensitivity of the method. For determination of blood factors, prothrombin, labeled fibrinogen, fibrinogen-coated containers, particularly microtiter plates, and one or more factor deficient plasmas may be provided for the detection of different factors. The various reagents, other than the fibrinogen-coated support, may be provided as lyophilized reagents, which may be reconstituted, and are provided in combination with buffers, stabilizers, inert proteins, such as serum albumins, or the like. For some applications, it may be desirable to lyophilize reagents in microtiter wells at concentrations appropriate for the assay. Where other than blood factors are involved, the kits may include the conjugate of the analyte and a molecule which modulates the activity of thrombin in combination of thrombin, in place of prothrombin. Other reagents may also be included in the kit, such as enzyme substrates and co-factors, where an enzyme is a label.

The following examples are offered by way of illustration and not by way of limitation.

EXPERIMENTAL

Fibrinogen-Peroxidase Conjugate

This was prepared by the method of Nakane and Kawaoi (J. Histochem. Cytochem (1974) 22:1084) using 40 mg of horseradish peroxidase and 300 mg of human fibrinogen. The molar ratio of peroxidase to fibrinogen in the final product was 0.39. This was diluted with unlabeled fibrinogen to a concentration of 0.72 mg/ml of fibrinogen with a molar ratio of 0.12 moles of peroxidase per mole of fibrinogen, stored in 50% glycerol at −20° C.

Thrombin Assay

In the first assay, microtiter plates were coated with 150 μl per well of 50 μg/ml of fibrinogen in 10 mM Tris-acetate buffered saline, pH 7.6 (TABS) containing 10 mM EDTA overnight at 4° C. The solution was removed from the plate, and 100 μl of a 10 μg/ml solution of peroxidase-fibrinogen in 3.8 mg/ml bovine serum albumin (BSA) in TABS containing 10 mM calcium chloride was added to the well. 50 μl of thrombin diluted from 0.1 to 0.00078 NIH units/ml (30–0.25 ng/ml) was added to each well for various times from 0–160 min, after which the solution was washed from the plate. Peroxidase assay was performed using orthophenylenediamine as the indicator dye, with 11 min of incubation. Optical density was measured at 490 nm using a microtiter plate reader, with the following results:

| [Thrombin] (NIH units/ml) | Incubation Time (min) | | | | | |
|---|---|---|---|---|---|---|
| | 0 | 10 | 20 | 40 | 80 | 160 |
| .033 | 0.41 | 0.52 | 1.24 | >2 | >2 | >2 |
| .017 | 0.31 | 0.30 | 0.91 | >2 | >2 | >2 |
| .0083 | 0.30 | 0.42 | 0.40 | 1.67 | >2 | >2 |
| .0042 | 0.23 | 0.22 | 0.26 | 0.87 | >2 | >2 |
| .0021 | 0.25 | 0.18 | 0.18 | 0.18 | 1.02 | >2 |
| .0010 | 0.22 | 0.15 | 0.18 | 0.23 | 0.37 | 1.55 |
| .0005 | 0.21 | 0.21 | 0.16 | 0.14 | 0.18 | 0.60 |
| .00026 | 0.20 | 0.24 | 0.19 | 0.25 | 0.32 | 0.24 |

Not only the endpoint (O.D.>2), but also the partial reaction (0.4>O.D.>2) can be used as a measure of thrombin activity. The penultimate value prior to the endpoint, or an approximate extrapolation to the concentration of thrombin yielding an O.D. value of 1 can be used to standardize this assay. For the above experiment, this value is reached at thrombin concentrations of:

| Incubation Time (min) | [Thrombin] for O.D. = 1 |
|---|---|
| 10 | >0.03 |
| 20 | 0.02 |
| 40 | 0.005 |
| 80 | 0.002 |
| 160 | 0.0008 |

In the next assay, benzamidine and D-phenylalanyl-L-prolyl-L-arginine chloromethyl ketone (PPACK) were added to thrombin at the start of the assay. Addition of these inhibitors increased the concentration of thrombin required to obtain equivalent binding of peroxidase-fibrin to the solid phase. The percent inhibition can be calculated from the increased thrombin concentration required to obtain equivalent activity, as % inhibition = 100 * (1-To/Ti)

where To is the thrombin concentration yielding an O.D.=1 in the absence of inhibitor, and Ti is the thrombin concentration yielding an O.D.=1 in the presence of a given inhibitor concentration. The inhibition by these two inhibitors, in an 80 min assay, is seen below:

| [PPACK], nM | % Inhibition | [Benzamidine], mM | % Inhibition |
|---|---|---|---|
| .005 | 11 | 0.5 | 8 |
| .01 | 19 | 1 | 41 |
| .02 | 43 | 2 | 55 |
| .05 | 62 | 5 | 75 |
| .1 | 79 | 10 | 84 |
| .2 | 83 | 20 | 97 |
| .5 | 95 | | |

The inhibition by these two inhibitors was consistent with their known affinities and mechanisms of action, as detailed in Markwardt et al. (*Eur. J. Biochemistry* (1968) (6:502; Kettner and Shaw, *Thrombosis Research* (1979) (14:969). The same approach could be used to measure inhibitor concentration of natural inhibitors of thrombin, such as antithrombin III. The concentration of inhibitor would be determined by a standard curve of inhibition using purified inhibitor, then obtaining equivalent inhibition of thrombin by the test sample. Testing several dilutions of inhibitor at a single thrombin concentration would appear to be the most convenient approach for measuring inhibitor concentration.

Measurement of Factor III (Thromboplastin, Tissue Factor)

In this study, the assay was modified to use normal human plasma as a substrate. Fibrinogen from normal plasma was precipitated with polyethylene glycol 1000 at a final concentration of 10%, as described in Masri et al. (*Thrombosis and Haemostasis* (1983) 49:116). The supernatant was mixed with an equal volume of 100% glycerol, and stored frozen at −70° C., or in liquid form at −20° C. For assay, 50 μl of diluted tissue factor in 20 mM calcium chloride, 1 mg/ml BSA, TABS was dispensed into the plate, followed by 100 μl per well of diluted plasma in 2 mM EDTA, 3.8 mg/ml BSA, 3.6 μg/ml peroxidase-fibrinogen, and 0.6% rabbit brain cephalin suspension in TABS. The endpoint of the assay was similar to that for thrombin, i.e., the concentration of thromboplastin which yielded an O.D. value of 1. The results obtained at different plasma concentrations and times of incubation are summarized below. The sensitivity of the assay was dependent on the substrate concentration and time of incubation, as expected. The limit of sensitivity was less than 1 ng/ml of crude brain thromboplastin protein.

Concentration of Human Brain Thromboplastin, in ng/ml of Crude Protein, Which Yields an O.D. Value of 1 at Different Plasma Concentrations and Incubation Times The assay was performed using four dilution series at each concentration of normal human plasma. Incubation was at 37° C.; assay of peroxidase was for 8 min at 37° C.

| Time (min) | Amount of Plasma Added Per Well (μl) | | | |
|---|---|---|---|---|
| | 0.1 | 0.2 | 0.4 | 0.8 |
| 40 | >355 | 148 ± 24 | 28 ± 3 | 4.3 ± 1 |
| 60 | 144 ± 27 | 15.3 ± 1.7 | 4.3 ± 1.0 | 0.7 ± 0.2 |
| 90 | 27 ± 4 | 5.7 ± 1.0 | 0.53 ± 0.17 | HB* |

*HB = high blank

The specificity of the assay was confirmed by repeating it in plasma substrates monodeficient in specific factors. Equivalent activity was obtained in normal plasma and in VIII, IX, XI and XII-deficient plasmas.

No activity (X and II deficient) or 100-fold lower activity (V and VII deficient) was measurable in substrate plasmas deficient in extrinsic or common pathway deficient factors.

Assay of Leukocyte Tissue Factor

In this assay, the tissue factor activity of monocytes isolated from peripheral blood of normal subjects was measured both before and after incubation in culture medium. The data are normalized for the number of cells present in the assay well which yielded an O.D. of 1 for the tissue factor assay. Leukocytes were isolated from citrated blood by centrifuging buffy coat cells over a Ficoll-hypaque layer and collecting the interface cells. Cells are incubated in a tissue culture medium consisting of 1 x RPMI, 25 mM HEPES, 1 x penicillin and streptomycin and 0.5% lactoalbumin hydrolyzate. The same cells were tested without incubation and after incubation for several hours or overnight (16 hr). A dramatic induction of tissue factor activity was measured, as seen below.

Levels of tissue factor in leukocytes isolated from peripheral blood. Data is expressed as the number of cells per well isolated after the indicated incubation time which yielded an O.D. value of 1 in a specific assay for tissue factor.

| Experiment 1 | | Experiment 2 | | Experiment 3 | |
|---|---|---|---|---|---|
| Hours | Cells/Well | Hours | Cells/Well | Hours | Cells/Well |
| 0 | 17874 | 0 | 120,000 | 0 | >125,000 |
| 4 | 57 | 2 | 2,314 | 1 | 41,666 |
| 16 | 1 | 16 | >1 | 16 | 6 |

The extraordinary sensitivity of this assay may be used in measuring tissue factor levels in isolated blood cells or other fractions. The assay appears able to measure the amount of tissue factor present in a single cell under some conditions. this could be of use in clinical testing for cells activated in vivo, or as an adjunct to cell sorting by identifying the population of cells containing tissue factor.

Other Extrinsic Pathway Factors

Measurement of other extrinsic pathway factors was accomplished by a modification of the assay in which 50 $\mu$l of diluted factors in 2 mM EDTA, 1 mg/ml BSA, TABS were placed in the well, 50 $\mu$l of diluted monodeficient plasmas in 2 mM EDTA-TABS containing 7.6 mg/ml BSA, 7.2 $\mu$g/ml peroxidase-fibrinogen and 1.2% rabbit brain cephalin suspension. The reaction was initiated by addition of 50 $\mu$l of tissue factor diluted in 1 mg/ml BSA, 20 mM calcium chloride, TABS. The table below shows the results for assay of factors VII and VIIa, in ng/ml of factors detectable at the appropriate plasma concentrations and incubation times.

Assay of Factors VII and VIIa in Factor VII-Deficient Plasma

Assays were performed as described above, using several plasma concentrations and incubation times. Four dilution series were assayed for each condition. The thromboplastin concentration was varied for each plasma concentration, as follows: 0.1 $\mu$l of plasma, 300 ng/ml thromboplastin; 0.2 $\mu$l, 120 ng/ml; 0.4 $\mu$l, 30 ng/ml; 0.8 $\mu$l, 9 ng/ml. Assay of peroxidase was for 8 min in each case. Data shown are the concentrations of factors VII or VIIa, in ng/ml in the final incubation mixture, which yields an O.D. value of 1 under these conditions.

| Factor | Time (min) | Amount of Plasma Per Well ($\mu$l) | | | |
|---|---|---|---|---|---|
| | | 0.1 | 0.2 | 0.4 | 0.8 |
| VII | 40 | >300 | 5.1 ± 1.7 | 1.2 ± 0.2 | .5 ± .2 |
| VII | 50 | .46 ± .21 | .18 ± .01 | .12 ± .02 | .09 ± .02 |
| VII | 90 | .06 ± .02 | .030 ± .006 | .026 ± .002 | HB* |
| VIIa | 40 | 6.3 ± 1.6 | .84 ± .19 | .41 ± .05 | .31 ± .03 |
| VIIa | 60 | .175 ± .006 | .050 ± .004 | .035 ± .003 | .039 ± .003 |
| VIIa | 90 | .022 ± .004 | .008 ± .002 | .0046 ± .0003 | HB* |

*HB = high blank

In the most sensitive assay in this series, less than 5 pg/ml of factor VIIa in 150 $\mu$l of sample can be measured. A similar high sensitivity for assay of factors II, X and V was obtained in comparable assays, using appropriate deficient plasmas.

This method is useful as well for assay of antibodies to clotting factors, and for using these antibodies to measure clotting factors. In the next assay, the ability of specific polyclonal rabbit antibodies to inhibit the activity of thrombin and Xa was measured. Antibody preparations were purified by absorption on columns of goat anti-rabbit IgG-Agarose and elution in 0.5 M acetic acid, or on columns of factors II- or X-Agarose and elution in 0.025 M citratesodium citrate, pH 3. These antibody preparations were diluted to final protein concentrations of 3-15 $\mu$g/ml, and tested for inhibition of thrombin and Xa. Thrombin assay was as described above. Xa assay was in a substrate consisting of a mixture of prothrombin, factor Va, peroxidase-fibrinogen, rabbit brain cephalin and BSA. The data is presented as the concentration of factor required to obtain an O.D. value of 1 in the presence of the indicated antibody.

| Antibody | Concentration $\mu$g/ml | Thrombin NIH units/ml | Xa ng/ml |
|---|---|---|---|
| Anti-X pur. on X-Agar. | 5.4 | .0065 | >240 |
| Anti-II pur. on II-Agar. | 3.3 | .035 | <2 |
| Anti-VII pur. on Goat anti-Rab | 14.3 | .0062 | <2 |
| Anti-X pur. on goat anti-Rab | 15.3 | .007 | 90 |
| Anti-II pur. on Goat anti-Rab | 14 | .016 | <2 |

Antibody to factor II inhibited thrombin by 60–80% at these concentrations, and antibody to factor X was more than 98% inhibitory. The inhibition was specific for the appropriate antigen, and was related to the purity of the antibody since specific affinity-purified antibody was more inhibitory than the IgG from the same immunized animal.

In addition to inhibition of a specific factor, antibodies which bind to epitopes which do not affect factor activity can be used in conjunction with the specific clotting assay to assay very low concentrations of these activated factors. As an example of this, in the next assay we determined the binding of factor Xa to a monoclonal antibody reactive with factor X. In this assay, microtiter plates coated with goat anti-mouse IgG were incubated with 0.9–667 ng/ml of monoclonal antibody and 0.16–20 ng/ml of factor Xa for 16 hr at 4° C. The plates were washed, and a factor Xa specific substrate consisting of factor II, factor Va, BSA, and rabbit brain cephalin was added to the plate and incubated at 37° C. for 40 and 60 min. Thrombin generated in this assay was measured by transferring 50 $\mu$l of the mixture into an assay plate containing peroxidase fibrinogen and BSA in TABS buffer. After 40 min of incubation, the plates were washed and bound peroxidase measured. The optical density values obtained in this case were:

| [Xa], mg/ml | 40 min of incubation: [Monoclonal Antibody], ng/ml | | | | | | |
|---|---|---|---|---|---|---|---|
| | 667 | 222 | 74 | 25 | 8.2 | 2.7 | Blank |
| 20 | 1.97 | >2 | >2 | >2 | 1.59 | .30 | .10 |
| 10 | 1.92 | >2 | >2 | 1.97 | 1.07 | .13 | .10 |
| 5 | >2 | >2 | >2 | >2 | .293 | .10 | .10 |
| 2.5 | 1.92 | >2 | >2 | 1.82 | .15 | .12 | .11 |
| 1.25 | 1.13 | 1.34 | 1.24 | .19 | .19 | .15 | .13 |
| 0.625 | .74 | .88 | .56 | .14 | .12 | .12 | .14 |
| 0.3125 | .34 | .44 | .17 | .15 | .14 | .14 | .13 |

| [Xa], ng/ml | 60 min of incubation: [Monoclonal Antibody], ng/ml | | | | | | |
|---|---|---|---|---|---|---|---|
| | 222 | 74 | 25 | 8.2 | 2.7 | 0.9 | Blank |
| 5 | >2 | >2 | >2 | >2 | >2 | >2 | 1.13 |
| 2.5 | >2 | >2 | >2 | >2 | 1.66 | 0.55 | .28 |
| 1.25 | >2 | >2 | >2 | 1.51 | .68 | .28 | .24 |
| 0.625 | >2 | >2 | >2 | .91 | .33 | .34 | .19 |
| 0.313 | >2 | >2 | 1.95 | .98 | .22 | .16 | .16 |
| 0.156 | 1.62 | 1.7 | 1.13 | .21 | .16 | .15 | .17 |

The sensitivity of this combined solid-phase immunoassay and solid-phase coagulation assay is high; less than 0.2 ng per ml of factor Xa could be detected in 0.15 ml of sample, or approximately 23 pg of Xa per sample. This would make the use of Xa or other activated clotting factors of special significance in sensitive immunoassays. The immunochemical reaction with activated clotting factor conjugated to antigen or antibody could be performed in an assay medium in which both appropriate antibody and fibrinogen were attached to the solid phase, and the subsequent assay for bound clotting factor would then result in attachment of labeled fibrinogen. Any group which can be covalently coupled to an antigen or antibody to assist in detection of immunochemical complexes could as well be attached to fibrinogen. The advantage of the combined use of clotting factor conjugates with subsequent coagulation cascade reactions amplifying the amount of reportable ligand attached to the solid phase is that sensitivity of detection is less limiting. For each molecule of activated factor bound, a large number of molecules of fibrin-conjugate will become bound to the solid phase. Low concentrations of clotting factor conjugate are employed in the immunoassay, which has advantages in competitive immunoassay design and the cost of using this assay technique. The sensitivity can be further enhanced by employing factors which are active earlier in the coagulation cascade, such as factor VIIa or tissue factor.

Although the foregoing invention has been described in some detail by way of illustration and example for purposes of clarity of understanding, it will be obvious that certain changes and modifications may be practiced within the scope of the appended claims.

What is claimed is:

1. In a method for determining the presence of a member of a specific binding pair capable of forming a binding complex, the improvement which comprises employing as at least a part of a detection system fibrinogen bound to a substrate and labeled fibrinogen, where with other than thrombin as the analyte, thrombin is added to the media.

2. A method according to claim 1, wherein said label is a enzyme.

3. A method according to claim 1, wherein said label is a fluorescer.

4. A method according to claim 1, wherein said analyte is a blood clotting factor.

5. A method according to claim 1, wherein said analyte is a clotting inhibitor or activator.

6. A method for detecting the presence of a blood factor involved in blood clotting other than fibrinogen or prothrombin which comprises:

combining a sample suspected of containing at least one blood clotting factor to be assayed as the analyte with prothrombin, labeled fibrinogen and fibrinogen bound to a surface in the presence of any additional blood factors necessary for the formation of thrombin from prothrombin;

incubating the mixture for a sufficient time for fibrin to form and initiate at least partial deposition of the labeled fibrinogen; and detecting the amount of label bound to the surface or in the supernatant as a measure of the amount of analyte in the sample.

7. A method according to claim 6, wherein said label is an enzyme.

8. A method according to claim 7, wherein said enzyme is peroxidase.

9. A method according to claim 6, wherein said blood factor is a factor of from V to XII.

10. A method according to claim 6, wherein said factor is a clotting inhibitor or activator.

* * * * *